(12) United States Patent
Trivedi

(10) Patent No.: US 10,245,096 B2
(45) Date of Patent: Apr. 2, 2019

(54) PRESSURE RELIEF SYSTEM FOR USE WITH GAS-ASSISTED MINIMALLY INVASIVE SURGICAL DEVICES

(71) Applicant: Covidien LP, Mansfield, MA (US)

(72) Inventor: Amit Trivedi, Upper Saddle River, NJ (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 15/602,929

(22) Filed: May 23, 2017

(65) Prior Publication Data

US 2017/0340376 A1 Nov. 30, 2017

Related U.S. Application Data

(60) Provisional application No. 62/341,554, filed on May 25, 2016.

(51) Int. Cl.

| | |
|---|---|
| *A61B 18/08* | (2006.01) |
| *A61M 13/00* | (2006.01) |
| *A61M 1/00* | (2006.01) |
| *A61B 18/00* | (2006.01) |
| *A61B 18/14* | (2006.01) |
| *A61B 90/00* | (2016.01) |

(52) U.S. Cl.
CPC ........ *A61B 18/082* (2013.01); *A61B 18/1482* (2013.01); *A61M 13/003* (2013.01); *A61B 2018/00589* (2013.01); *A61B 2018/00595* (2013.01); *A61B 2018/00601* (2013.01); *A61B 2018/00922* (2013.01); *A61B 2018/00958* (2013.01); *A61B 2090/064* (2016.02); *A61B 2218/005* (2013.01); *A61B 2218/007* (2013.01); *A61M 2205/3344* (2013.01)

(58) Field of Classification Search
CPC .............. A61M 1/0035; A61M 13/003; A61M 1/0066; A61B 2018/00595; A61B 2018/00589; A61B 18/1482; A61B 2018/00958; A61B 2218/005; A61B 2018/00601

See application file for complete search history.

(56) References Cited

U.S. PATENT DOCUMENTS

| | | | |
|---|---|---|---|
| 2,708,933 | A | 5/1955 | August |
| 2,808,833 | A | 10/1957 | August |
| 2,828,748 | A | 4/1958 | August |
| 3,991,764 | A | 11/1976 | Incropera et al. |
| 4,274,070 | A | 6/1981 | Thiene |
| 4,562,838 | A | 1/1986 | Walker |
| 4,781,175 | A | 11/1988 | McGreevy et al. |

(Continued)

OTHER PUBLICATIONS

U.S. Appl. No. 62/075,897, filed Nov. 6, 2014, Amit Triveti.
U.S. Appl. No. 62/341,554, filed May 25, 2016, Amit Trivedi.

*Primary Examiner* — Theodore Stigell

(57) ABSTRACT

An electrosurgical device is adapted for use through a port and within a body cavity. The device includes a gas supply supplying gas to a distal tip and a valve to regular such supply, and an electric supply for supplying electricity to the distal tip. A pressure relief system is provided to regulate an outflow of gas from within the body cavity to prevent exceeding a predetermined pressure. The inflow of the gas through the valve and outflow of gas through the pressure relief system may occur simultaneously.

15 Claims, 7 Drawing Sheets

(56) References Cited

U.S. PATENT DOCUMENTS

| | | | |
|---|---|---|---|
| 5,098,430 A | 3/1992 | Fleenor | |
| 5,217,457 A | 6/1993 | Delhuerga et al. | |
| 5,256,138 A | 10/1993 | Burek et al. | |
| 5,306,238 A | 4/1994 | Fleenor | |
| 5,312,400 A | 5/1994 | Bales et al. | |
| 5,344,548 A | 9/1994 | Alberti et al. | |
| 5,376,089 A | 12/1994 | Smith | |
| 5,449,356 A * | 9/1995 | Walbrink | A61B 18/1482 606/37 |
| 5,480,397 A | 1/1996 | Eggers et al. | |
| 5,541,376 A | 7/1996 | Ladtkow et al. | |
| 5,593,406 A | 1/1997 | Eggers et al. | |
| 5,702,387 A | 12/1997 | Arts et al. | |
| 5,720,745 A | 2/1998 | Farin et al. | |
| 5,951,548 A | 9/1999 | DeSisto et al. | |
| 6,076,392 A | 6/2000 | Drzewiecki | |
| 6,197,026 B1 | 3/2001 | Farin et al. | |
| 6,250,132 B1 | 6/2001 | Drzewiecki | |
| 6,266,995 B1 | 7/2001 | Scott | |
| 6,272,905 B1 | 8/2001 | Drzewiecki | |
| 6,305,212 B1 | 10/2001 | Drzewiecki | |
| 6,348,051 B1 | 2/2002 | Farin et al. | |
| 6,458,125 B1 | 10/2002 | Cosmescu | |
| 6,723,091 B2 | 4/2004 | Goble et al. | |
| 6,747,218 B2 | 6/2004 | Huseman et al. | |
| 6,958,063 B1 | 10/2005 | Soll et al. | |
| 7,150,747 B1 | 12/2006 | McDonald et al. | |
| 7,296,571 B2 | 11/2007 | Foltz et al. | |
| 7,303,559 B2 | 12/2007 | Peng et al. | |
| 7,537,594 B2 | 5/2009 | Sartor | |
| 7,585,295 B2 | 9/2009 | Ben-Nun | |
| 8,241,278 B2 | 8/2012 | Sartor | |
| 2003/0052792 A1 | 3/2003 | Koyano et al. | |
| 2004/0034339 A1 | 2/2004 | Stoller et al. | |
| 2004/0129270 A1 | 7/2004 | Fishman | |
| 2004/0138658 A1 | 7/2004 | Farin et al. | |
| 2004/0167512 A1 | 8/2004 | Stoddard et al. | |
| 2004/0181220 A1 | 9/2004 | Farin | |
| 2005/0015086 A1 | 1/2005 | Platt | |
| 2005/0021021 A1 | 1/2005 | Foltz et al. | |
| 2005/0187537 A1 | 8/2005 | Loeb et al. | |
| 2006/0036239 A1 | 2/2006 | Canady | |
| 2006/0052774 A1 | 3/2006 | Garrison et al. | |
| 2006/0069387 A1 | 3/2006 | Gedebou | |
| 2006/0178667 A1 | 8/2006 | Sartor et al. | |
| 2009/0076505 A1 | 3/2009 | Arts | |
| 2014/0276717 A1 | 9/2014 | Wan et al. | |
| 2016/0128756 A1 | 5/2016 | Trivedi | |
| 2016/0128757 A1 | 5/2016 | Trivedi et al. | |

\* cited by examiner

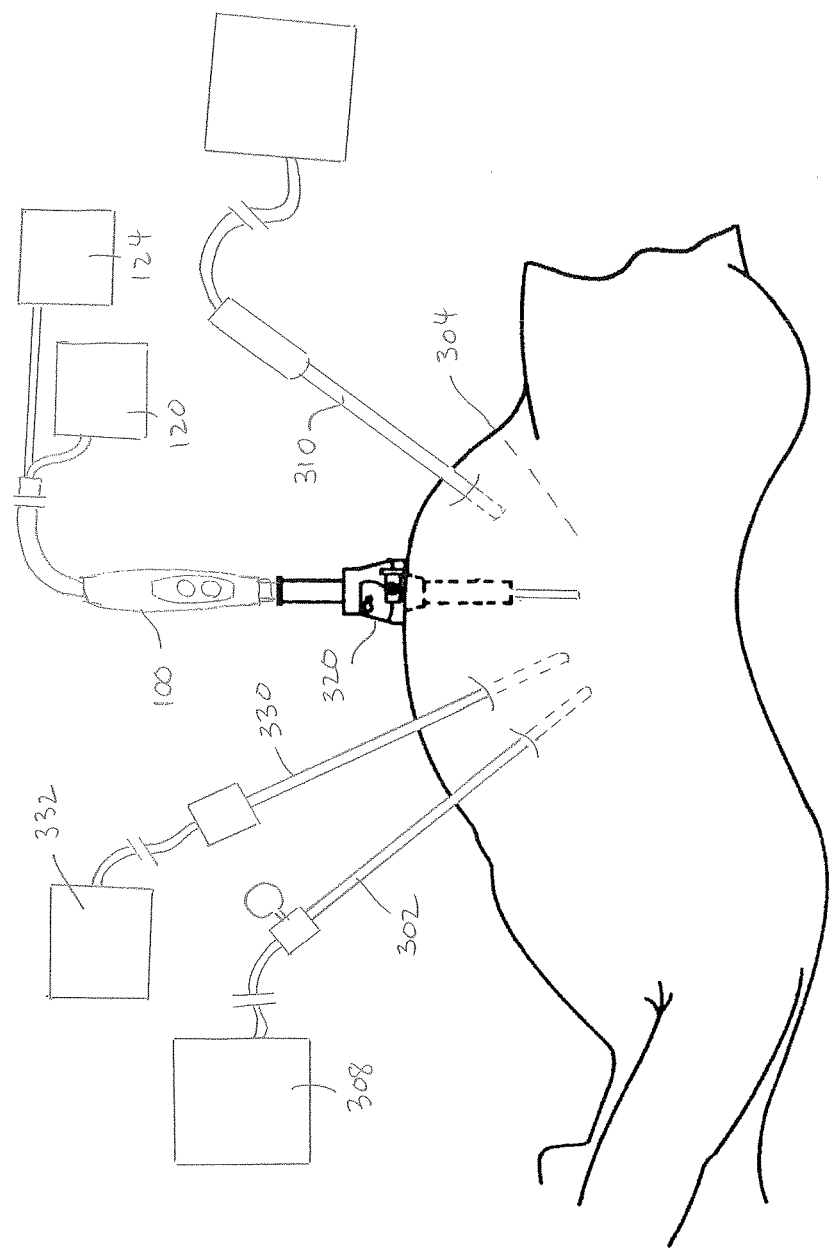

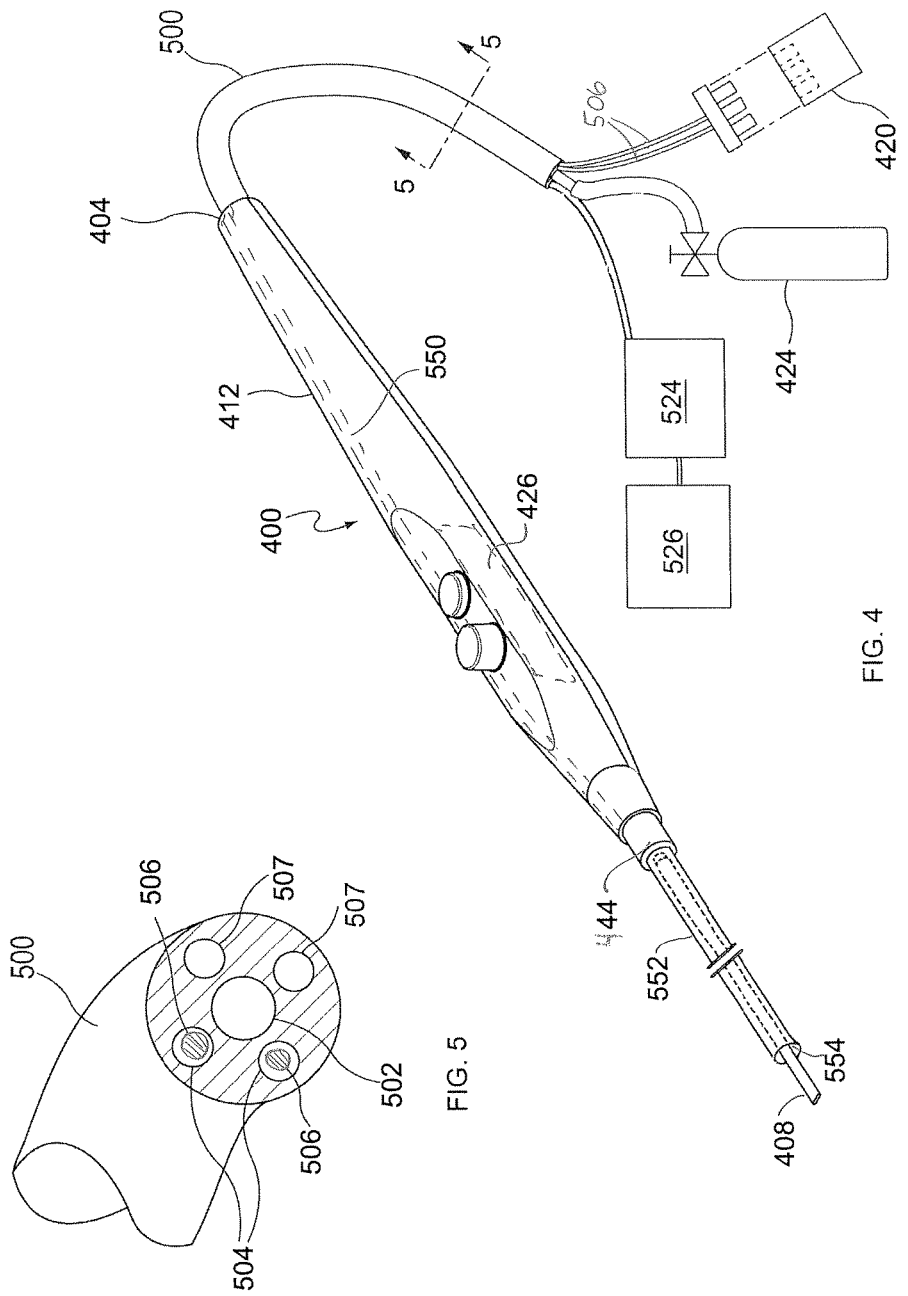

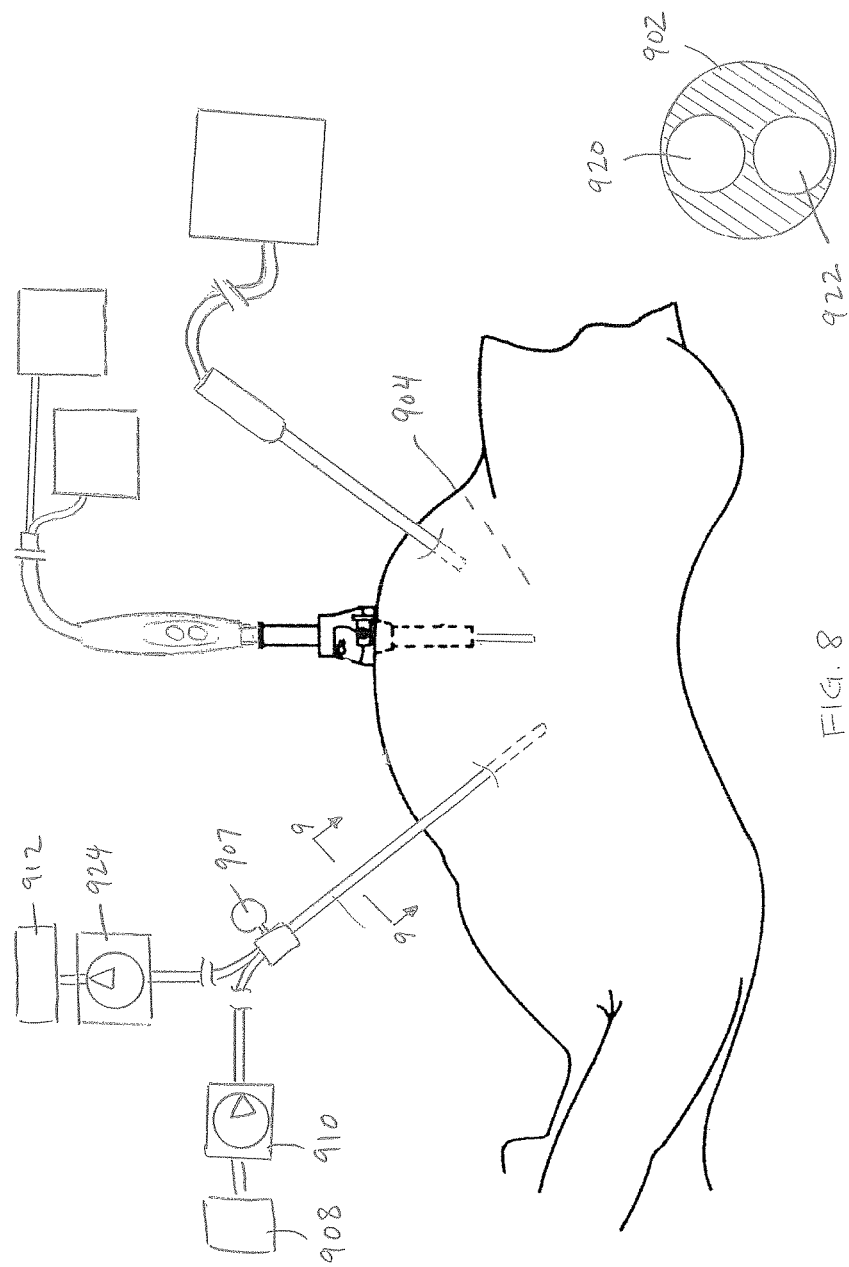

PRESSURE RELIEF SYSTEM FOR USE WITH GAS-ASSISTED MINIMALLY INVASIVE SURGICAL DEVICES

CROSS REFERENCE TO RELATED APPLICATIONS

This application claims the benefit of U.S. Provisional Ser. No. 62/341,554, filed May 25, 2016, which is hereby incorporated by reference herein.

This application is related to U.S. Ser. No. 14/955,962, filed Dec. 1, 2015, which is a continuation-in-part of U.S. Ser. No. 14/615,763, filed Feb. 6, 2015, which claims the benefit of priority under 35 U.S.C. § 119(e) to provisional application 62/075,897, filed on Nov. 6, 2014, the entire contents of which are incorporated herein by reference in their entireties.

BACKGROUND

1. Field

The present invention relates to surgical systems, and particularly to valves used in surgical systems.

2. State of the Art

Cautery devices have been used in surgical procedures to perform cutting and coagulation of tissue and blood vessels. Typically, cautery devices are "pen"-like devices that a surgeon can grasp by the hand to use. The cautery device typically is connected to an electrical generator that outputs a level of current that is conducted to a tip of the device to achieve the desired cutting and/or coagulation effect during a surgical procedure.

The use of cautery devices on tissue results in the generation of smoke and vapor, which are unwanted byproducts that reduce visibility in the area of the tip. Also, cautery devices have the potential to provide enough energy to cause fires in an operating room environment, which is typically a high oxygen environment. Approximately 500 operating room fires occur in the United States each year, the vast majority of which are related to a cautery device.

In response to these concerns, co-owned US Publ. No. 20160128756 and 20160128757, herein incorporated by reference herein, have taught a cautery device that inhibits fire at a surgical site. The cautery device includes a handpiece extending axially from a proximal end to a distal end and a cautery tip extending coaxially with the handpiece from the distal end of the handpiece. The tip defines a coaxial channel extending from the handpiece and along a length of the cautery tip from a proximal open end to a distal open end. The device includes a gas supply connection extending from the proximal end of the handpiece for supplying an inert gas, such as carbon dioxide, to the cautery tip. The gas supply connection is fluidly coupled to the cautery tip. The device includes an electric supply connection extending from the proximal end of the handpiece for supplying electricity to the cautery tip. The electric supply connection is electrically coupled to the cautery tip. The inert gas supplied to the cautery tip is introduced to the channel at the proximal open end and exits the tip at the distal open end.

The infused inert gas operates to provide several advantages. The flow of inert gas reduces the opportunity for ignition of tissue and reduces generation of smoke. The flow of inert gas removes debris from about the surgical site. The controlled flow of inert gas increases visualization of the surgical site.

While the described cautery device has certain advantages in open surgery, it is not necessarily adapted to a laparoscopic abdominal or thoracic surgical procedure performed within a body cavity and through a surgical port. Such procedures utilize insufflation of the body cavity to maintain a working space within the body. Once the body cavity is insufflated with gas, the surgical environment is not adapted to unmetered infusion of additional gas, which would occur through use of the described cautery device. The body cavity may become over-pressurized through use of the cautery device.

SUMMARY

A cautery device includes a handpiece extending axially from a proximal end to a distal end, a shaft extending from the distal end of the handpiece, and a cautery tip extending coaxially with the handpiece from the distal end of the handpiece. The shaft has sufficient length to extend through a trocar port. The handpiece and shaft may be unitarily constructed or integrated. The tip extends from the shaft and defines a coaxial channel extending from the handpiece and along a length of the cautery tip from a proximal open end to a distal open end. The device includes a gas supply connection extending from the proximal end of the handpiece for supplying gas to the cautery tip. The gas supply connection is fluidly coupled to the cautery tip. The device includes an electric supply connection extending from the proximal end of the handpiece for supplying electricity to the cautery tip. The electric supply connection is electrically coupled to the cautery tip. The gas supplied to the cautery tip is introduced to the channel at the proximal open end and exits the tip at the distal open end.

The instrument is inserted through a surgical port into the peritoneal or thoracic cavity. The peritoneal or thoracic cavity is subject to positive pressure via an insufflation instrument inserted into the body cavity. A pressure relief system is provided for relieving pressure within the body cavity. The pressure relief system may be located at the insufflation instrument, a separate instrument or port, or through the cautery device. The pressure release system may be in the form of a valve that passively or actively releases pressure. The pressure release system may be active in the form of vacuum system that actively decreases pressure within the body cavity.

As the cautery is used, inert gas is infused at or adjacent the cautery tip. Should the intra-cavity pressure exceed a set maximum pressure, the pressure relief system is operated to release pressure from within the body cavity.

BRIEF DESCRIPTION OF THE DRAWINGS

FIG. 3 is a schematic view of the human body, and another plurality of minimally invasive surgical instruments, including a gas-assisted cutting instrument and another pressure relief system, performing a surgical procedure on the human body.

FIG. 4 shows an embodiment of a gas-assisted cautery device at least partially incorporating a pressure relief system.

FIG. 5 shows a cross-section through a multi-lumen tubing coupled at the proximal end of the gas-assisted cautery device of FIG. 4.

FIG. 8 is a schematic view of the human body, and yet another plurality of minimally invasive surgical instruments, including a gas-assisted cutting instrument and another pressure relief system, performing a surgical procedure on the human body.

FIG. 9 is an enlarged cross-section view across line 9-9 in FIG. 8.

DETAILED DESCRIPTION

Figure 1:
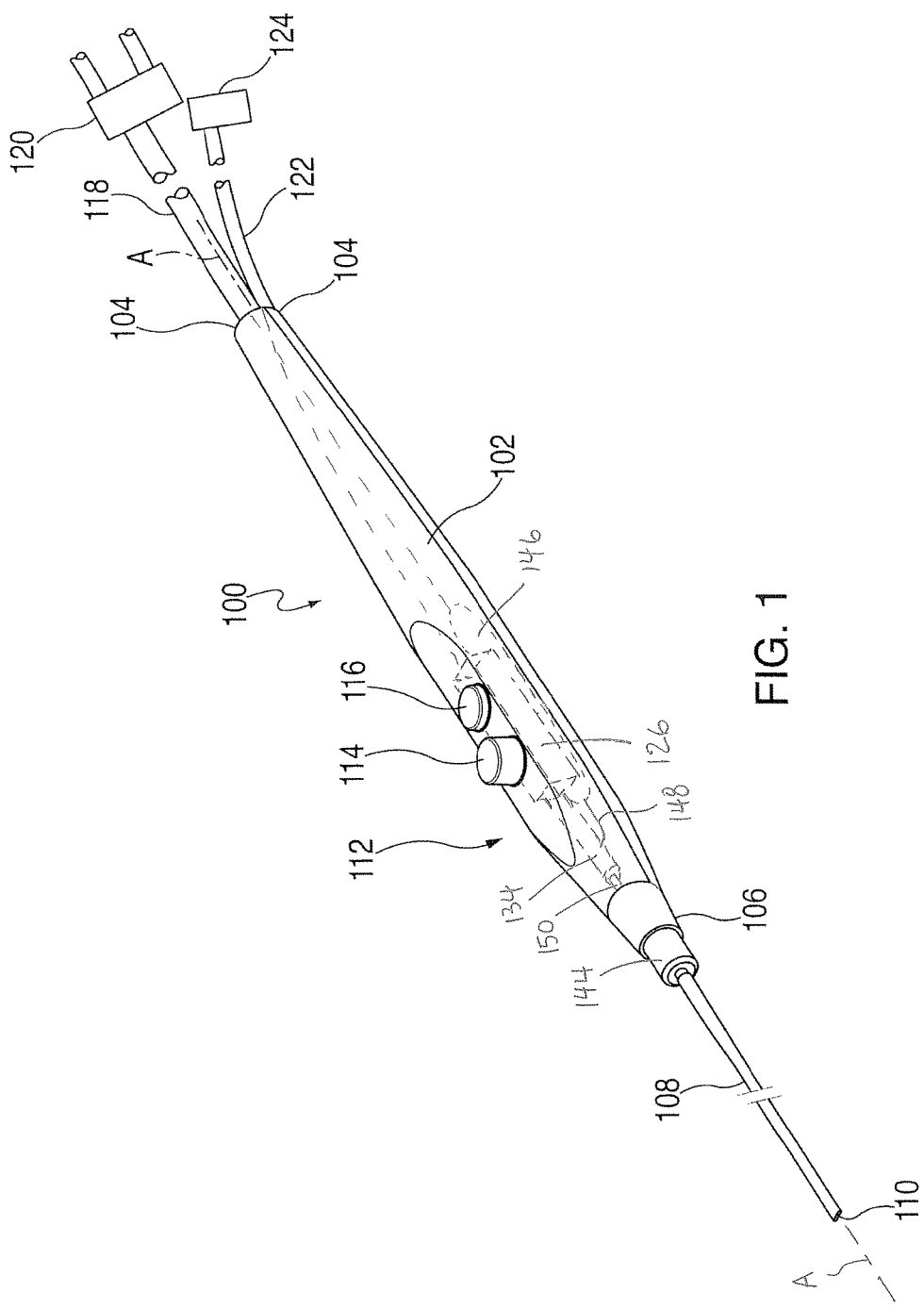
FIG. 1 is an isometric view of an embodiment of a gas-assisted cautery device adapted for a minimally invasive surgical procedure surgery.

Turning now to FIG. 1, an embodiment of a gas-assisted cautery device 100 is shown. The cautery device 100 includes an elongated housing 102 that extends longitudinally along an axis A-A from a proximal end 104 to a distal end 106. The device 100 also includes a removable hollow cautery tip 108 that extends longitudinally from the housing coaxially with axis A-A. The cautery tip 108 may define an open channel 110 that extends at least partially through the tip 108. The open channel 110 is preferably coaxial with the axis A-A. The housing 102 defines a handpiece 112 that is arranged so that it may be grasped in a user's hand like a writing instrument to direct the cautery tip 108 during a surgical procedure while also allowing a user of the device 100 to actuate buttons 114, 116 that extend from the housing 102. As will be described in greater detail below, the cautery tip 108 receives electric power to operate the tip 108 so that it can be used to perform various cautery tool procedures, such as cutting and coagulation. Also, the cautery device 100 is constructed to selectively permit gas to flow to be dispensed adjacent the tip of the cautery tip 108; e.g., through the open channel 110 of the cautery tip 108, or through one or more radial openings adjacent the tip.

The cautery device 100 is operated in various modes in response to selective actuation of one or more of the buttons 114, 116, as will be described in greater detail below. Each of the buttons 114, 116 may operate the cautery device 100 in a corresponding mode of operation, such as a coagulation mode and a cutting mode. Also, one or more of the buttons 114, 116 may be a multi-function button. For example, each respective button 114, 116 may be arranged to both control a gas flow of a gas through the cautery tip 108, as well as control power output to the cautery tip 108 based on the mode of operation corresponding to each button 114, 116. More specifically, in one embodiment, a first button 114 may correspond to the cutting mode and a second button 116 may correspond to the coagulation mode. In such an embodiment, selectively actuating the first button 114 may set a first gas flow rate through the cautery tip 108 and a power level corresponding to the cutting mode, while selectively actuating the second button 116 may set a second gas flow rate to the cautery tip 108 and a power level corresponding to the coagulation mode. Thus, a user of the device 100 may select the operating mode of the device by selecting and pressing a corresponding button 114, 116. Detailed construction and operation of the power regulation, via an electrical unit 146, and gas flow regulation, via an internal valve train 126, are described in detail in previously incorporated US Publ. No. 20160128756 and 20160128757.

A power cord 118 and a gas delivery tube 122 extend from the proximal end 104 of the cautery device 100. The power cord 118 supplies electric power to the device 100 from an electric power supply 120. The gas tube 122 supplies an inert gas to the device 100 from a source of pressurized gas 124. The inert gas is preferably carbon dioxide, but may also be nitrogen.

The cautery tip 108 is removably coupled in a collet 144 that is provided at the distal end of the handpiece 112. The cautery tip 108 extends through the collet 144. More specifically, when the cautery tip 108 is fully coupled to the handpiece 112, the cautery tip 108 is fluidly coupled to the valve train 126 and is electrically coupled to an electrical unit 146.

In the embodiment shown in FIG. 1, the cautery tip 108 has a generally cylindrical, proximal portion 150 that extends through the collet 144 and to the fluid and electrical couplers 134, 148. The cautery tip has a length that is sufficient and suitable to use during a minimally invasive procedure. That is, the length is adapted to extend from outside the human body, through a trocar port or other body port, and to the tissue of interest that is to be acted upon. The cautery tip 108 is removably coupled to the handpiece 112 to facilitate tip replacement and interchanging different cautery tips (e.g., with different forms) with the same handpiece 112. To provide such interchangeability, the electrical and fluid couplers 148 and 134 may be constructed as removable couplers, such as a fluid quick-connect coupler and an electrical socket, respectively.

The electrical unit 146 is electrically connected to the wire 118. The electrical unit 146 controls the flow of electrical power to the tip 108 to operate the device 100 in one of its operating modes through actuation of the aforementioned buttons 114, 116.

The button 114 may be used to operate the device 100 in a cutting mode and button 116 may be used to operate the device 100 in a coagulation mode. A surgeon may press button 114 to simultaneously open a first valve of valve train 126 to allow for the gas to flow at a first flow rate to the tip 108 and to energize a first circuit of electrical unit 146 to supply electrical energy to the tip 108 sufficient for operating the device 100 in a cutting mode. Similarly, a surgeon may press the second button 116 to open a second valve of valve train 126 to allow for a second gas flow rate to the cautery tip 108 and to simultaneously energize a second circuit of electrical unit 146 to supply electrical energy to the tip 108 sufficient for operating the device 100 in a coagulation mode. The first and second flow rates may be the same or different based on the operating mode selected by pressing the associated buttons 114, 116. The first and second flow rates are sufficient to supply the gas at least in a quantity to the open end of the tip 108 to create a zone about the tip which displaces fluid from tissue and increases visibility. Also, while flammability is not as great a concern in a closed surgical procedure, particularly where the body cavity operated within may be filled with a non-flammable insufflation gas, it is appreciated that the region adjacent the cautery tip 108 is provided with increase flame resistance when the tissue is subject to cautery. Also, each of the first and second flow rates may be variable based on the range of motion (distance the button is depressed) of the switch button.

Figure 2:
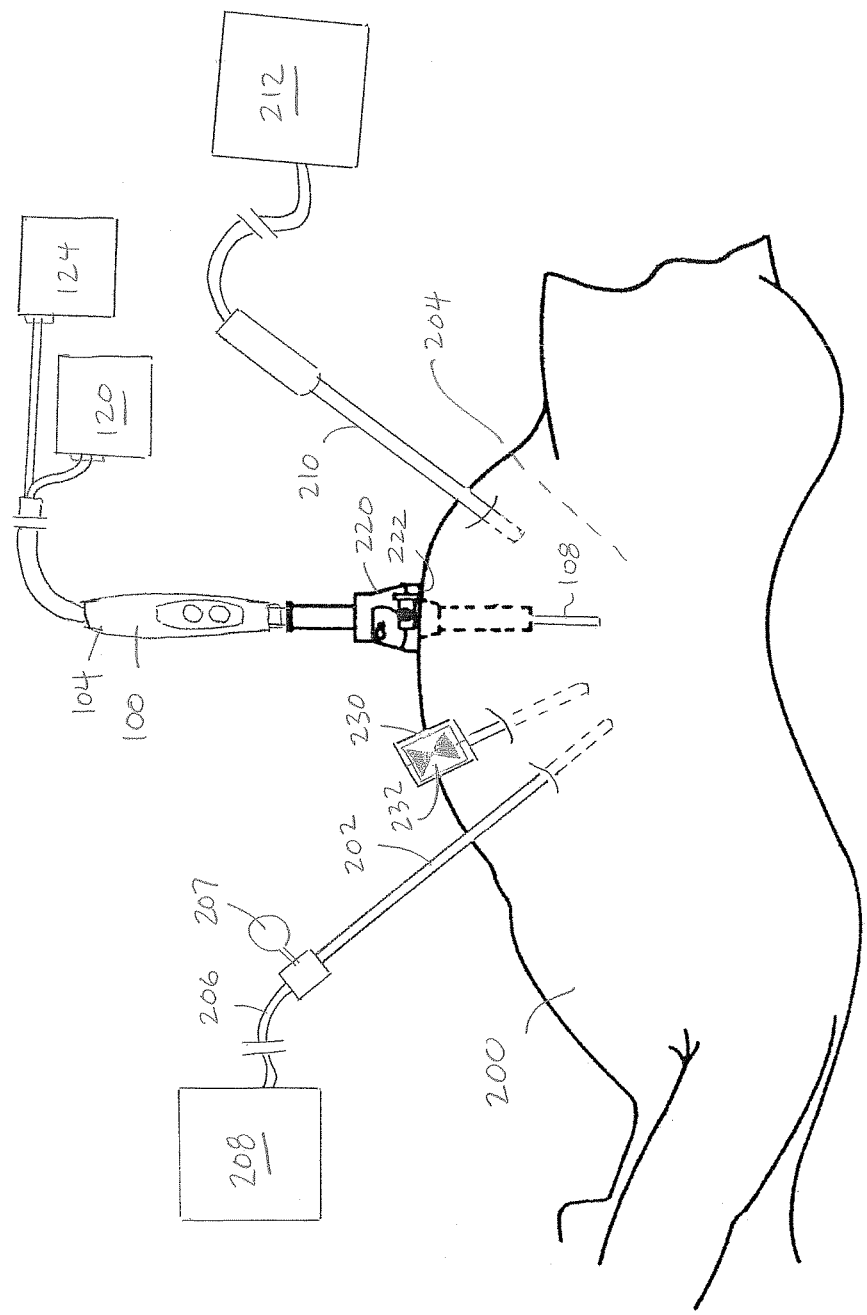
FIG. 2 is a schematic view of a human body, and a plurality of minimally invasive surgical instruments, including a gas-assisted cutting instrument and a pressure relief system, performing a surgical procedure on the human body.

Referring now to FIG. 2, instruments for use during a minimally invasive surgical procedure on a human body 200 are shown. An insufflation lumen 202 is advanced into the abdominal cavity 204. The insufflation lumen 202 is coupled with a flexible tube 206 to a source 208 of inert gas, such as carbon dioxide, to provide positive pressure to inflate the abdominal cavity to a first pressure and thereby expand the abdominal cavity to define a working space. A typical first pressure may be in the range of 10 to 20 mmHg and more typically 15 mmHg. A pressure sensor 207 may communicate with the lumen 202 so that in the event that there is a pressure drop below the first pressure, (i) an alarm will signal (i.e., to advise surgical staff to manually add inflation gas), (ii) gas from source 208 will be automatically added into the abdominal cavity to raise the pressure, or (iii) both. A laparoscope 210 is advanced into the abdominal cavity 204. The laparoscope 210 includes an optical imaging system that outputs an image from within the abdominal cavity 204 to a monitor 212 for viewing by the surgical staff. A trocar port or other port 220 is inserted through a surgical incision 222 and into the body to provide port access to the abdominal cavity 204. The cautery device 100 is inserted within the port 220. The proximal end 104 of the cautery device 100 is coupled to the electric power supply 120 and the source of inert gas 124. Inert gas sources 124 and 208 may be the same source or independent sources. The cautery tip 108 extends through the port 220 such that it can be manipulated to act on tissue. A pressure relief device 230 is inserted through the tissue and into the abdominal cavity 204. The pressure relief device 230 is separate from, and may be positioned at a location displaced from, the cautery device 100. The pressure relief device 230 includes a valve 232 that is normally closed but which automatically opens to vent the abdominal cavity upon reaching a higher threshold second pressure, and automatically closes once a third pressure lower than the second pressure is reached. The second pressure is preferably within +2 mmHg of the first pressure, and the third pressure is preferably between 0 and −2 mmHg relative to the first pressure. This allows are relatively narrow pressure window to be maintained. Other pressure windows are considered within the scope of the disclosure. The valve 232 is preferably passive, but may be actively opened via activation from a pressure sensor (not shown) to release pressure. The third pressure is a pressure at or above the first pressure so that abdominal cavity insufflation is maintained.

During the procedure it is assumed that the abdominal cavity will be inflated and maintained at the first pressure. Then, as the gas-assisted cautery device is operated, inert gas is further supplied to the abdominal cavity through the cautery device. Depending on at least (1) the amount of liquid and debris covering tissue which the surgeon wants to clear away with the injected gas through the device, and (2) the amount of gas supplied during cauterization, significant additional inert gas may be injected into the inflated abdominal cavity. In order to prevent overpressure of the cavity, when such additional gas causes the inert gas pressure within the abdominal cavity to reach the threshold second pressure, the valve 232 automatically opens to release the gas until the pressure is under the defined threshold. The valve 232 is preferably configured to permit a steady release that permits fluid outflow at a rate greater than gas inflow from the cautery device 100; however, the valve 232 may have a fail-safe mode that permits rapid release (a greater gas-release opening size), e.g., in the event pressure is at a dangerous level to the patient, or at an option of the surgical staff.

Turning now to FIG. 3, another system, similar to the system shown in FIG. 2 (with like elements having reference numerals incremented by 100 relative thereto), is shown with respect to use on a human body during a minimally invasive surgical procedure. The system includes insufflation lumen 302 coupled to an inert gas source 308, a laparoscope 310, a port 320, and a cautery device 100 insertable within the port 320 and coupled to the electric power supply 120 and the source of inert gas 124. A pressure relief device 330 is inserted through the tissue also into the abdominal cavity 304. The pressure relief device 330 is separate from, and may be positioned at a location displaced from, the cautery device 100. The pressure relief device 330 is coupled to a vacuum source 332. The pressure relief device 330 activates the vacuum source to apply vacuum pressure to actively reduce intra-abdominal inflation when the abdominal cavity is inflated to the threshold second pressure. The pressure relief device 330 automatically stops application of vacuum pressure once a third pressure lower than the second pressure is reached. The third pressure is a pressure at or above the first pressure so that suitable abdominal cavity insufflation is maintained. The pressure relief device 330 may activate at a second pressure different from the second pressure of the relief device 230, and the pressure relief device may stop activation at a third pressure different from the third pressure of the relief device 230.

Referring now to FIGS. 4 and 5, another system to prevent over-pressurization of the intra-body cavity when using a gas-assisted surgical device is shown. The system includes a gas-assisted surgical cautery device 400. Cautery device 400 is substantially similar to cautery device 100, with the variations noted as follows. The handpiece 412 of the device 400 includes a vacuum lumen 550 separate from and without fluid communication with the valve train 426 through which inert gas is injected from the inert gas source 424 to the cautery tip 408. The cautery tip 408 is surrounded along a portion of its length with a pressure-relief collar 552 that extends from the collet 444 at the distal end 406 of the handpiece toward the distal tip of the cautery tip so that it reaches inside the body cavity during a surgical procedure. The annulus 554 between the vacuum collar 552 and the cautery tip 408 is in fluid communication with the vacuum lumen 550. The proximal end of the handpiece 412 may be coupled to a multilumen flexible tube 500 that accommodates, in lumen 502 the inert gas inflow (from gas supply 424), in lumen 504 the electrical cables 506 (from the power source power supply 420), and in lumen 507 vacuum application (from vacuum source 526). Thus, the cautery device 400 at least partially integrates the pressure relief system. A pressure sensor 524 is preferably coupled in communication between the pressure-relief collar 552 and the vacuum source 526 to sense the pressure within the body cavity, and activate the vacuum source when pressure exceeds a threshold pressure. Upon activation from the pressure sensor 524, vacuum source 526 activates to apply vacuum pressure to actively reduce intra-abdominal inflation. The vacuum source 526 automatically stops application of vacuum once a third pressure lower than the second pressure is reached. The third pressure is a pressure at or above a preset first pressure for insufflation so that suitable abdominal cavity pressure is maintained. The vacuum source 526 may be activated at a second pressure different from the second pressures of the relief devices 230, 330, and the vacuum source may stop activation at a third pressure different from the third pressures of the relief devices 230, 330.

Figure 6:
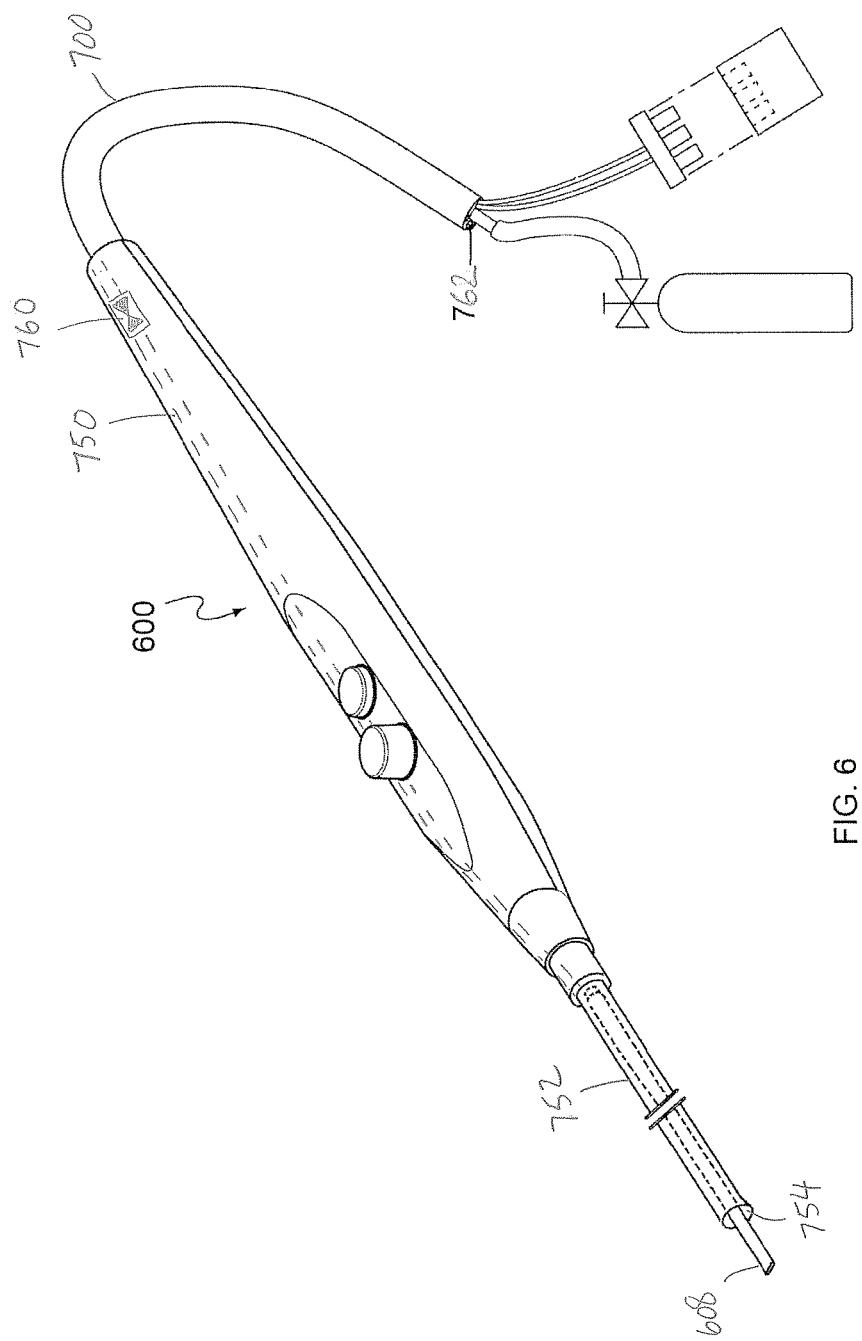
FIG. 6 shows another embodiment of a gas-assisted cautery device at least partially incorporating a pressure relief system.

Referring now to FIG. 6, another system, similar to the system shown in FIGS. 4 and 5 (with like elements having reference numerals incremented by 100 relative thereto), is shown. In addition to features shown with respect to FIGS. 4 and 5, the cautery device 600 includes a one-way passive valve 760 inline with the lumen 750 extending through the handpiece and in fluid communication with the annulus 754 between the cautery tip 608 and the pressure relief collar 752. A lumen of the flexible tube 700 in communication with the valve 760 opens to atmosphere at 762. The valve 760 may be, by way of example, a slit valve or duckbill valve. The valve 760 is adapted to automatically open when the pressure upstream of the valve (e.g., within the annulus) exceeds the predetermined second pressure, and automatically closes again when the pressure is reduced to be at or below the third pressure.

Figure 7:
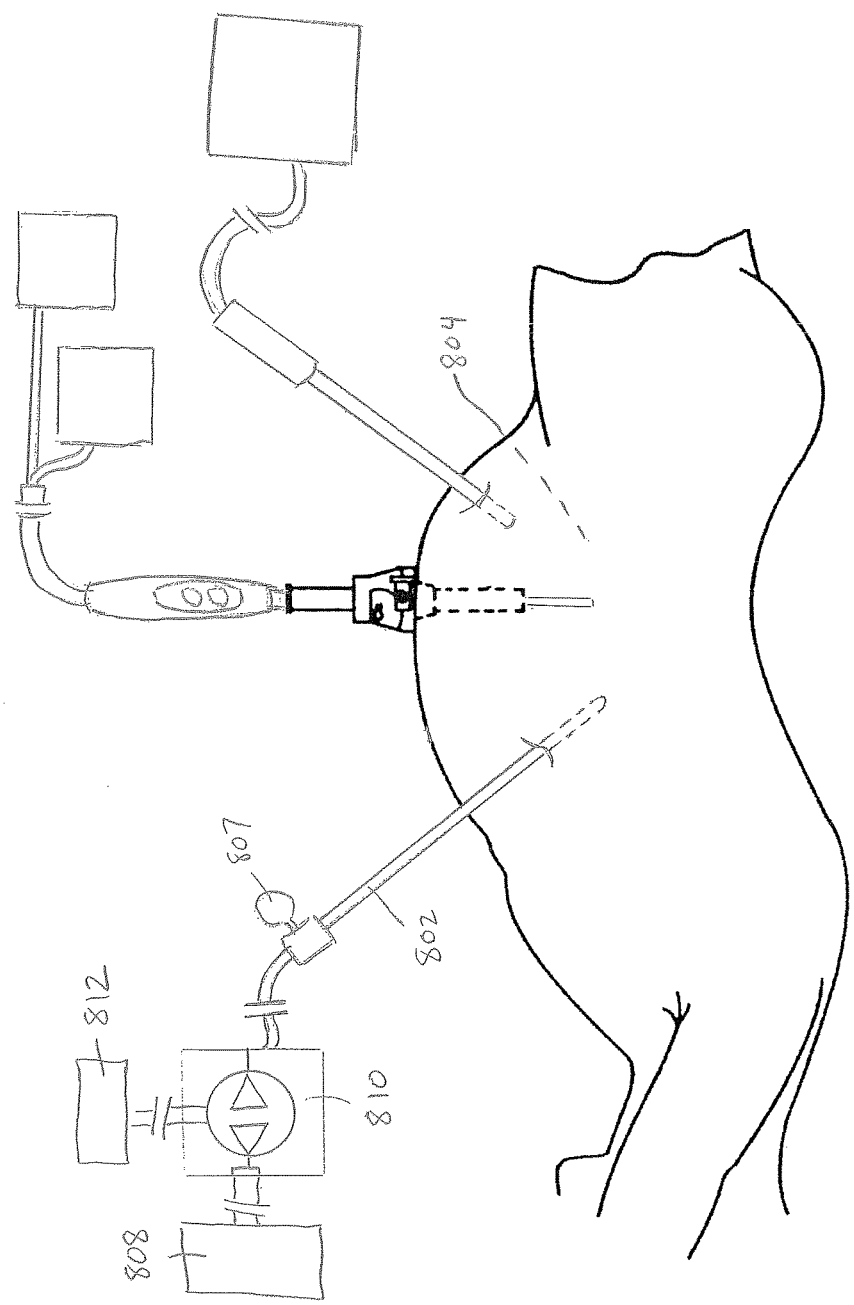
FIG. 7 is a schematic view of the human body, and another plurality of minimally invasive surgical instruments, including a gas-assisted cutting instrument and another pressure relief system, performing a surgical procedure on the human body.

Turning now to FIG. 7, another system, similar to the system shown in FIG. 3 is shown. In accord with the system of FIG. 7, the insufflation tube 802 includes a bidirectional pump 810 that is adapted to both (i) pump insufflation gas from a gas supply 808 into the body cavity 804, and (ii) evacuate gas from the body cavity to atmosphere or a store 812. The directional operation of the pump (inflow or outflow) is determined by the pressure sensor 807. When the pressure sensor senses pressure below the first pressure, gas is pumped to the body cavity; when the pressure sensor senses pressure above the first pressure, air is evacuated from the body cavity.

Turning now to FIGS. 8 and 9, another system, similar to the system shown in FIG. 7 is shown. In accord with the system of FIGS. 8 and 9, the insufflation tube 902 is a multilumen tube including an insufflation lumen 920 and an evacuation lumen 922. Insufflation lumen is coupled to a pump 910 adapted to pump insufflation gas from a gas supply 908 into the body cavity 904. Evacuation lumen 922 is coupled to either a passive valve (not shown) or an evacuation pump 924 adapted to remove overpressure gas from the body cavity to atmosphere or a store 912. When a pressure sensor 907 senses pressure below the first pressure, insufflation pump 910 is operated to pump insufflation gas into the body cavity 904. When the pressure sensor 907 senses pressure above the first pressure, evacuation pump 924 removes gas from the body cavity. When pressure sensor 907 may be a single sensor or a plurality of sensors.

There have been described and illustrated herein several systems for pressure relief in association with gas-assisted minimally invasive electrosurgical instruments. While one embodiment of the system has been described with respect to the electrosurgical instrument of a gas-assisted cautery device, it is not intended that the invention be limited thereto, as it is intended that the invention be as broad in scope as the art will allow and that the specification be read likewise. Thus, the system also pertains to argon-plasma devices, devices that include a combination of cautery and argon-plasma, and other gas-assisted electrosurgical devices. Also, while in various embodiments a pressure sensor has been disclosed coupled to an active pressure relief device, it is appreciated that the pressure sensor may be located displaced and separate from the active pressure vacuum device, but nonetheless signal activation of the pressure relief device. Also, while carbon dioxide is a preferred inert gas, it will be recognized that other gases that are non-flammable may be used. Also, while the system has been generally described with respect to surgical procedure within the abdominal cavity, it is appreciated that the system is equally applicable to other body cavities during minimally invasive surgical procedures. By way of example only, the systems and methods herein are applicable to closed thoracic surgical procedures. Moreover, the features of the several embodiments described herein can be used together (mixed and matched), without limitation. It will therefore be appreciated by those skilled in the art that yet other modifications could be made to the provided invention without deviating from its scope as claimed.

What is claimed is:

1. A method of performing a minimally invasive procedure on a human body, comprising:
    a) inserting an insufflation tube through a first surgical incision through tissue and into a body cavity;
    b) insufflating the body cavity with gas under pressure through the insufflation tube;
    c) inserting a working end of an electrosurgical instrument through a second surgical incision through the tissue and into the body cavity,
    d) delivering gas from a gas supply to a distal tip of the electrosurgical instrument
    e) delivering electrosurgical energy from an electrosurgical energy source to the distal tip while delivering the gas to the distal tip to treat tissue in the body cavity;
    f) inserting a pressure relief device through a third surgical incision through the tissue and into the body cavity; and
    g) automatically releasing gas from within the body cavity via the pressure relief device when gas pressure within the body cavity exceeds a predetermined pressure.

2. The method according to claim 1, wherein automatically releasing gas from within the body cavity includes automatically releasing gas via the pressure relief device at a location separate from the insufflation tube and the electrosurgical instrument.

3. The method according to claim 1, wherein automatically releasing gas from within the body cavity includes opening a normally-closed valve of the pressure relief device.

4. The method according to claim 1, wherein the gas delivered from the gas supply to the distal tip is carbon dioxide.

5. The method according to claim 1, further comprising:
    inserting a trocar through the second surgical incision prior to inserting the working end of the electrosurgical instrument through the second surgical incision; and
    inserting the working end of the electrosurgical instrument through the inserted trocar and into the body cavity.

6. The method according to claim 1, wherein insufflating the body cavity includes delivering gas from the gas supply through the insufflation tube and into the body cavity.

7. The method according to claim 1, wherein insufflating the body cavity includes delivering gas from an additional gas supply independent from the gas supply delivering gas to the distal tip of the electrosurgical instrument.

8. The method according to claim 1, further comprising sensing a pressure within the body cavity via a pressure sensor coupled to the insufflation tube.

9. The method according to claim 8, further comprising:
    opening a valve of the pressure relief device to release gas from the body cavity based on a first threshold pressure sensed by the pressure sensor; and
    closing the valve of the pressure relief device to prevent release of gas from the body cavity based on a second threshold pressure sensed by the pressure sensor.

10. The method according to claim 1, further comprising adjusting at least one valve disposed in the electrosurgical instrument to control a flow rate of the gas delivered from the gas supply to the distal tip.

11. A method of performing minimally invasive surgery, comprising:

forming a first surgical incision through tissue at a first location of an abdominal cavity;

inserting an insufflation device through the first surgical incision and into the abdominal cavity;

delivering gas to the abdominal cavity via the insufflation device to insufflate the abdominal cavity;

forming a second surgical incision through tissue at a second location of the abdominal cavity;

inserting a trocar through the second surgical incision and into the abdominal cavity;

inserting at least a portion of an electrosurgical instrument through the inserted trocar and into the abdominal cavity;

forming a third surgical incision through tissue at a third location of the abdominal cavity;

inserting a pressure relief device through the third surgical incision and into the abdominal cavity;

simultaneously delivering gas and electrosurgical energy to the inserted electrosurgical instrument for treating tissue in the abdominal cavity;

sensing a pressure within the abdominal cavity via a pressure sensor; and releasing gas from the abdominal cavity through the pressure relief device based on the pressure sensed by the pressure sensor.

12. The method according to claim 11, further comprising delivering gas to the inserted electrosurgical device and the abdominal cavity via the insufflation device from a common source of gas.

13. The method according to claim 11, further comprising:

delivering gas to the inserted electrosurgical device from a first source of gas; and delivering gas to the abdominal cavity via the insufflation device from a second source of gas independent from the first source of gas.

14. The method according to claim 11, further comprising:

opening a valve of the pressure relief device to release gas from the abdominal cavity based on a first threshold pressure sensed by the pressure sensor; and closing the valve of the pressure relief device to prevent release of gas from the abdominal cavity based on a second threshold pressure sensed by the pressure sensor.

15. The method according to claim 11, further comprising adjusting at least one valve disposed in the electrosurgical instrument to control a flow rate of the gas delivered to the inserted electrosurgical instrument.

* * * * *